United States Patent
Hirai et al.

(10) Patent No.: US 9,230,322 B2
(45) Date of Patent: Jan. 5, 2016

(54) IMAGE PROCESSOR, TREATMENT SYSTEM, AND IMAGE PROCESSING METHOD

(71) Applicant: KABUSHIKI KAISHA TOSHIBA, Tokyo (JP)

(72) Inventors: Ryusuke Hirai, Shinagawa Tokyo (JP); Yukinobu Sakata, Kawasaki Kanagawa (JP); Yasunori Taguchi, Kawasaki Kanagawa (JP); Takeshi Mita, Yokohama Kanagawa (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 14/677,142

(22) Filed: Apr. 2, 2015

(65) Prior Publication Data

US 2015/0287189 A1 Oct. 8, 2015

Related U.S. Application Data

(60) Provisional application No. 61/975,003, filed on Apr. 4, 2014.

(30) Foreign Application Priority Data

Jul. 8, 2014 (JP) ................... 2014-140601

(51) Int. Cl.
  *G06K 9/00* (2006.01)
  *G06T 7/00* (2006.01)
  (Continued)

(52) U.S. Cl.
  CPC .............. *G06T 7/0012* (2013.01); *A61N 5/107* (2013.01); *A61N 5/1049* (2013.01); *G06T 3/40* (2013.01);
  (Continued)

(58) Field of Classification Search
  None
  See application file for complete search history.

(56) References Cited

U.S. PATENT DOCUMENTS 6,792,074 B2 * 9/2004 Erbel et al. ............... 378/65
7,756,567 B2 7/2010 Kuduvalli et al.
(Continued)

FOREIGN PATENT DOCUMENTS

JP 2007-282877 11/2007
JP 2010-508895 3/2010
(Continued)

OTHER PUBLICATIONS

Tomazevic et al., "3-D/2-D Registration by Integrating 2-D Information in 3-D," IEEE Transactions on Medical Imaging, vol. 25, No. 1, Jan. 2006, pp. 17-27.
(Continued)

*Primary Examiner* — Bhavesh Mehta
*Assistant Examiner* — Amandeep Saini
(74) *Attorney, Agent, or Firm* — Nixon & Vanderhye, P.C.

(57) ABSTRACT

According to some embodiments, an image processor includes an image acquirer, a first image generator, a point acquirer, a detector, a calculator and a determiner. The detector detects a second plurality of points in the first perspective images or the second perspective images corresponding to the first plurality of points. The calculator calculates, based on at least the first plurality of points and the second plurality of points, a difference in position of the target between when the first perspective images were captured and when the second perspective images were generated. The determiner determines whether or not the difference is in a range. If the difference is not in the range, then the first image generator generates updated ones of the second perspective images from an updated one of the volume data, which is different by the difference from a previous one of the volume data.

19 Claims, 8 Drawing Sheets

(51) Int. Cl.
  *G06T 3/40* (2006.01)
  *G06T 15/08* (2011.01)
  *A61N 5/10* (2006.01)

(52) U.S. Cl.
  CPC ......... *G06T 15/08* (2013.01); *A61N 2005/1061* (2013.01); *G06T 2207/10004* (2013.01); *G06T 2207/10016* (2013.01); *G06T 2207/10081* (2013.01); *G06T 2207/30004* (2013.01); *G06T 2207/30196* (2013.01); *G06T 2215/16* (2013.01)

(56) References Cited

U.S. PATENT DOCUMENTS

| | | | |
|---|---|---|---|
| 7,894,649 | B2 | 2/2011 | Fu et al. |
| 8,457,372 | B2 | 6/2013 | Fu et al. |
| 2013/0188856 | A1 | 7/2013 | Adler, Jr. et al. |
| 2015/0045605 | A1 | 2/2015 | Hirai et al. |

FOREIGN PATENT DOCUMENTS

| | | |
|---|---|---|
| JP | 2011-212130 | 10/2011 |
| JP | 2012-020009 | 2/2012 |
| JP | 2013-099431 | 5/2013 |
| JP | 2015-029838 | 2/2015 |

OTHER PUBLICATIONS

Markelj et al., "Robust Gradient-Based 3-D/2-D Registration of CT and MR to X-Ray Images," IEEE Transactions on Medical Imaging, vol. 27, No. 12, Dec. 2008, pp. 1704-1714.

Tamaki, Toru, "Pose Estimation and Rotation Matrices," IEICE Technical Report, SIP2009-48, 2009, pp. 59-64, and concise explanation in English.

Iikura, Takahiko, "Toshiba's Advanced Technologies Contributing to Heavy-Ion Radiotherapy for Cancer Treatment," Toshiba Review, vol. 68, No. 1, 2013, pp. 2-6, and concise explanation in English.

\* cited by examiner

IMAGE PROCESSOR, TREATMENT SYSTEM, AND IMAGE PROCESSING METHOD

CROSS-REFERENCE TO RELATED APPLICATION

This application is based upon and claims the benefit of priority from Japanese Patent Application No. 2014-140601, filed Jul. 8, 2014, and the benefit of U.S. Provisional Application No. 61/975,003, filed Apr. 4, 2014, the entire contents of which are incorporated herein by reference.

FIELD

Embodiments described herein relate generally to an image processor, a treatment system, and an image processing method.

BACKGROUND

In radiotherapy, heavy ion (heavy particle) radiotherapy, and the like, a lesion is treated by irradiating it with radiation or heavy ion radiation, thereby destroying the lesion. When performing radiotherapy or heavy ion radiotherapy, it is difficult to achieve effective treatment effect unless the radiation or heavy ion radiation is irradiated precisely on the lesion. For this reason, CT (computed tomography) is used to image the target of the treatment (for example, the object to be treated) to gain an understanding of the position of the lesion in three dimensions. A physician or technician determines a treatment plan that includes the angle and radiation strength of irradiation of radiation or heavy ion radiation, based on the determined three-dimensional position of the lesion. When actual treatment is done, positioning is performed to align the position of the object to be treated at the time of treatment with the position of the object to be treated at the time the treatment plan was determined. Because treatment is performed a plurality of times based on the treatment plan, positioning is performed each time. It is necessary that the object to be treated maintains its attitude from the start of the positioning to the end of the treatment, so that it is desirable that the positioning be performed in a short period of time. However, because the positioning must be done precisely, it may be difficult to perform positioning in a short period of time.

DETAILED DESCRIPTION

Figure 1:
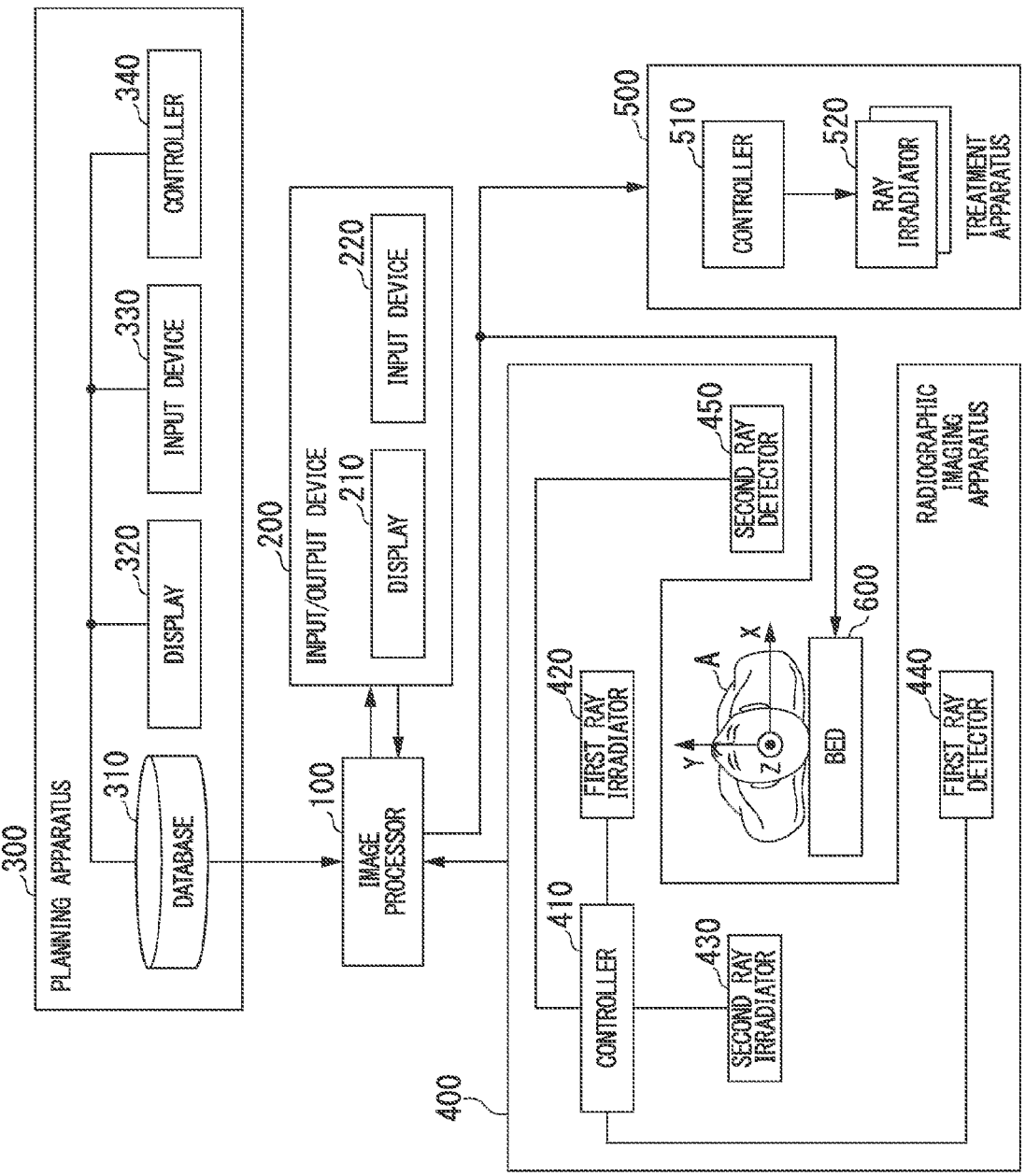
FIG. 1 is a block diagram illustrating the configuration of a treatment system in accordance with a first embodiment.

According to some embodiments, an image processor may include, but is not limited to, an image acquirer, a first image generator, a point acquirer, a detector, a calculator and a determiner. The image acquirer acquires a plurality of first perspective images, which have been captured from a target in at least two mutually different directions. The first image generator generates from volume data of the target a plurality of second perspective images in the at least two mutually different directions. The point acquirer acquires a first plurality of points in one of the first perspective images and the second perspective images. The detector detects a second plurality of points in the second perspective images corresponding to the first plurality of points if the first plurality of points is present in the first perspective images. The detector detects a second plurality of points in the first perspective images corresponding to the first plurality of points if the first plurality of points is present in the second perspective images. The calculator calculates, based on at least the first plurality of points and the second plurality of points, a difference in position of the target between when the first perspective images were captured and when the second perspective images were generated. The determiner determines whether or not the difference is in a range. If the difference is not in the range, then the first image generator generates updated ones of the second perspective images from an updated one of the volume data, which is different by the difference from a previous one of the volume data. If the difference is not in the range, then the detector detects an updated one of the second plurality of points in one of the first perspective images and the updated ones of the second perspective images. If the difference is not in the range, then the calculator calculates the difference based on at least the first plurality of points and the updated one of the second plurality of points.

In some cases, the determiner calculates a similarity between the first perspective images and the second perspective images. The determiner determines whether or not the similarity calculated is at least a pre-established threshold to determine whether or not the difference is in the range.

In some cases, the determiner calculates a similarity between the partial images including the first plurality of points or the second plurality of points in the first perspective images and the second partial images including the first plurality of points or the second plurality of points in the second perspective images. The determiner determines whether or not the similarity calculated is at least a pre-established threshold to determine whether or not the difference is in the range.

In some cases, the determiner determines the difference is the range if the calculator has calculated the difference a prescribed number of times.

In some cases, the determiner determines the prescribed number of times based on an image contrast of at least one of the first perspective images and the second perspective images.

In some cases, the determiner determines the prescribed number of times which is smaller as the image contrast is higher.

In some cases, the determiner identifies a tissue of the target, where a projected image of the tissue is included in at least one of the first perspective images and the second perspective images. The determiner determines the prescribed number of times in accordance with the tissue identified.

In some cases, the determiner calculates an area of bone in the projected target of at least one of the first perspective images. The second perspective image, and the determiner makes the prescribed number of times smaller as the area is larger.

In some cases, the determiner calculates the similarity between the first perspective images and the updated ones of the second perspective images. The determiner outputs the difference if the similarity calculated is lower than a similarity between the first perspective images and a previous ones of the second perspective images.

In some cases, the image acquirer performs smoothing of the first perspective image.

In some cases, the image acquirer makes a change in resolution of the first perspective images to make the projected image of the tissue in the first perspective image be identical in dimension with the projected image of the tissue in the second perspective image.

In some cases, the processor may further include, but is not limited to, a second image generator. The second image generator receives the first plurality of points from the point acquirer, the second plurality of points from the detector, the first perspective images form the image acquirer and the second perspective images from the first image generator. The second image generator generates image data in which the first plurality of points, the second plurality of points, the first perspective images and the second perspective images.

According to other embodiments, a treatment system may include, but is not limited to, a radiographic imaging apparatus, an image processor and a display. The radiographic imaging apparatus captures a plurality of first perspective images of a target from at least mutually different directions. The processor may include, but is not limited to, an image acquirer, a first image generator, a point acquirer, a detector, a calculator and a determiner. The image acquirer acquires the plurality of first perspective images from the radiographic imaging apparatus. The first image generator generates from volume data of the target a plurality of second perspective images in the at least two mutually different directions. The point acquirer acquires a first plurality of points in one of the first perspective images and the second perspective images. The detector detects a second plurality of points in the second perspective images corresponding one-to-one to the first plurality of points if the first plurality of points is present in the first perspective images. The detector that detects a second plurality of points in the first perspective images corresponding one-to-one to the first plurality of points if the first plurality of points is present in the second perspective images. The calculator calculates, based on at least the first plurality of points and the second plurality of points, a difference in position of the target between when the first perspective images were captured and when the second perspective images were generated. The determiner determines whether or not the difference is in a range. If the difference is not in the range, then the first image generator generates updated ones of the second perspective images from an updated one of the volume data, which is different by the difference from a previous one of the volume data. If the difference is not in the range, then the detector detects an updated one of the second plurality of points in one of the first perspective images and the updated ones of the second perspective images. If the difference is not in the range, then the calculator calculates the difference based on at least the first plurality of points and the updated one of the second plurality of points. The display displays the first perspective images and the second perspective images.

In some cases, the target volume data is acquired by imaging the target using an X-ray CT apparatus.

In some cases, the system may include, but is not limited to, a second image generator and an input device. The second image generator generates image data in which the first plurality of points and the second plurality of points are overlaid onto the first perspective images and the second perspective images. The second image generator supplies the image data to the display. The input device receives instructions, and gives the image processor the instructions to correct a position of at least one of the second plurality of points in the image displayed by the display. The image processor makes the calculator calculate an updated one of the second plurality of points based on the instructions. The calculator calculates the difference based on at least the first plurality of points and the updated on of the second plurality of points.

In some cases, the system may include, but is not limited to, one or more irradiators. The irradiator irradiates radiation to the target.

In some cases, the system may include, but is not limited to, a bed and a treatment apparatus. The bed may include, but is not limited to, a movable mount for the target. There is the treatment apparatus for irradiating the target with radiation. The bed receives the difference from the image processor. The bed, based on the difference, moves the movable mount for irradiation to the target.

According to still other embodiments, an image processing method may include, but is not limited to, the following processes. A plurality of first perspective images, which have been captured from a target in at least two mutually different directions, is acquired. A plurality of second perspective images in the at least two mutually different directions is generated from volume data of the target. A first plurality of points in one of the first perspective images and the second perspective images is acquired. A second plurality of points is detected in at least one of: a) the second perspective images corresponding to the first plurality of points if the first plurality of points is present in the first perspective images; and b) the first perspective images corresponding to the first plurality of points if the first plurality of points is present in the second perspective image. Based on at least the first plurality of points and the second plurality of points, the difference is calculated by calculating a difference in position of the target between when the first perspective images were captured and when the second perspective images were generated. It is determined whether or not the difference is in a range. Updated ones of the second perspective images are generated from an updated one of the volume data, which is different by the difference from a previous one of the volume data, if the difference is not in the range. An updated one of the second plurality of points in one of the first perspective images and the updated ones of the second perspective images is detected, if the difference is not in the range. The difference is calculated based on at least the first plurality of points and the updated one of the second plurality of points, if the difference in not in the range.

According to furthermore embodiments, an image processor may further include, but is not limited to, a processor, and a memory that stores processor-executable instructions that, when executed by the processor, cause the processor to perform the following acts or operations. The processor generates from volume data of the target a second perspective images in the at least two mutually different directions. The processor detects a plurality of second points in one of first perspective images and the second perspective images corresponding to a first plurality of points. The first perspective images were captured from the target in the at least two mutually different directions. The first plurality of points indicates a plurality of positions in the target in one of the first perspective images and the second perspective images. The processor calculates, based on the first plurality of points and the second plurality of points, a difference in position of the target between when the first perspective images were captured and when the second perspective images were generated. The processor determines whether or not the difference is in a range. If the difference is not in the range, then the processor generates updated ones of the second perspective images from an updated one of the volume data, which is different by the difference from a previous one of the volume data. If the difference is not in the range, then the processor detects an updated one of the second plurality of points in one of the first perspective images and the updated ones of the second perspective images. If the difference is not in the range, then the processor calculates the difference based on at least the first plurality of points and the updated one of the second plurality of points.

Various Embodiments will be described hereinafter with reference to the accompanying drawings. In the following embodiments, elements to which the same reference numerals are applied perform the same operations and will sometimes not be repeatedly described.

First Embodiment

FIG. 1 is a block diagram illustrating the configuration of the treatment system 10 in the first embodiment. The treatment system 10 may include, but is not limited to, the image processor 100, an input/output device 200, and a radiographic imaging apparatus 400. The treatment system 10 may further include, but is not limited to, a planning apparatus 300, a treatment apparatus 500, and a bed 600. In the treatment system 10, based on a treatment plan established using the planning apparatus 300, a user such as a physician or technician operates the input/output device 200, the radiographic imaging apparatus 400, the treatment apparatus 500, and the bed 600 to treat a target A. The user operates the input/output device 200 based on second perspective images generated by the image processor 100 and first perspective images captured by the radiographic imaging apparatus 400.

The planning apparatus 300 establishes a treatment plan with respect to the target A to be subjected to radiotherapy, proton therapy, particle radiotherapy, heavy ion radiotherapy, or the like. The planning apparatus 300 establishes a treatment plan, based on information such as a captured image of the internal form of the target A and operations input by a user such as a physician or technician. The images used in the planning apparatus 300 are images captured by a radiographic imaging apparatus capable of viewing and capturing the inside of the target A. The radiographic imaging apparatus may be, but is not limited to, an X-ray imaging apparatus, a computed tomography (CT) apparatus, a magnetic resonance imaging (MRI) apparatus, a positron emission tomography (PET) apparatus, or a single photon emission computed tomography (SPECT) apparatus. The images used in the planning apparatus 300 may be either two-dimensional images or three-dimensional images. In the present embodiment, the description will be for the case of images based on volume data collected by an X-ray CT apparatus being used to establish a treatment plan.

The planning apparatus 300 may include, but is not limited to, a database 310, a display 320, an input device 330, and a controller 340. The database 310 has stored therein data obtained by imaging the target A. The data stored in the database 310 may be the voxel data itself obtained by imaging the target A, or may be voxel data after being subjected to correction processing, such as logarithmic conversion, offset correction, sensitivity correction, beam hardening correction, or scattered radiation correction with respect to the data obtained by imaging. In addition to voxel data, the database 310 may store a two-dimensional image reconstructed from voxel data. In the present embodiment, the voxel data in the database 310 will be described for the case of being stored as volume data.

The display 320 displays second perspective images, under the control of the controller 340. Second perspective images are digitally reconstructed radiographs (DRR), which are obtained by reconstructing voxel data stored in the database 310. In the first embodiment, the description will be for the case in which images to be used are perspective images of the target A viewed in a prescribed direction, that is, a simulated digitally reconstructed radiograph as second perspective images. The type of the second perspective images displayed by the display 320 corresponds to the type of images captured by the radiographic imaging apparatus 400. For example, if the radiographic imaging apparatus 400 is an X-ray imaging apparatus, the second perspective images displayed on the display 320 are DRR images resulting from simulating an image captured by an X-ray imaging apparatus.

The input device 330 receives instructions from a user, and gives the controller 340 the instructions. The controller 340, based on the instruction, controls the database 310, the display 320 and the input device 330 in the planning apparatus 300. The controller 340 may, for example, be implemented by one or more processors, and executes a program and the instructions to perform control operations based on the program and the instructions. The controller 340, based on information responsive to the second perspective image and the instructions, stores into the database 310 information indicating a position at which the target A is to be treated.

The radiographic imaging apparatus 400 is an X-ray imaging apparatus or the like, and views and captures an image of the inside of the target A when treatment is performed. The present embodiment will be described for the case of the radiographic imaging apparatus 400 being an X-ray imaging apparatus. The radiographic imaging apparatus 400 may include, but is not limited to, a controller 410, a first ray irradiator 420, a second ray irradiator 430, a first ray detector 440, and a second ray detector 450. The first ray detector 440 generates a first perspective image of the target A, based on an X-ray irradiated from the first ray irradiator 420 that has passed through the target A. The first ray detector 440 may include, but is not limited to, a flat panel detector (FPD). The FPD receives an X-ray that has passed through the target A and converts it to a digital signal. The first ray detector 440 generates the first perspective image based on the digital signal obtained from the FPD.

The second ray detector 450 generates another first perspective image viewing the target A, based on an X-ray irradiated from the second ray irradiator 430 that has passed through the target A. The second ray detector 450, similar to the first ray detector 440, may include, but is not limited to, an FPD. The second ray detector 450 generates the other first perspective image based on the digital signal obtained from the FPD.

The viewing direction in which the first ray detector 440 views the target A differs from that in which the second ray detector 450 views the target A. For example, the first ray irradiator 420, the second ray irradiator 430, the first ray detector 440, and the second ray detector 450 are disposed so that the imaging plane of the FPD of the first ray detector 440 and the imaging plane of the FPD of the second ray detector 450 are mutually perpendicular. The first ray detector 440 and the second ray detector 450 may each have an image intensifier (II) in place of the FPD.

The controller 410 controls the first ray irradiator 420, the second ray irradiator 430, the first ray detector 440, and the second ray detector 450 in the radiographic imaging apparatus 400. The controller 410 may, for example, be implemented by one or more processors, and executes a program to perform control operation based on the program. The controller 410 supplies the image processor 100 with the first perspective images of the target A The image processor 100 acquires from the radiographic imaging apparatus 400 the imaging parameters at the time the first perspective images of the target A were captured. The image processor 100 reads out from the database 310 of the planning apparatus 300 volume data that was used in establishing the treatment plan. The image processor 100, based on the imaging parameters, generates from the volume data a second perspective image from the viewing point that is the same as the viewing point when the radiographic imaging apparatus 400 captured the first perspective images of the target A.

The image processor 100 acquires from the input/output device 200 a first plurality of points in one of the first perspective images or second perspective images. The first plurality of points indicates a plurality of positions in the target A determined by the user. The user operates the input/output device 200 to establish the first plurality of points, based on the first perspective images and second perspective images displayed on the input/output device 200. If the first plurality of points has been established on the first perspective image, the image processor 100 detects the second plurality of points corresponding one-to-one to the first plurality of points in the second perspective images. If the first plurality of points has been established in the second perspective images, the image processor 100 detects the second plurality of points corresponding one-to-one to the first plurality of points in the first perspective images.

The second plurality of points is a plurality of center points of a plurality of partial images having the greatest similarity to partial images in a rectangular region of a prescribed size having the first plurality of points as its center. If the first plurality of points has been established in the first perspective images, the second plurality of points in the second perspective images is the center point of partial images having the greatest similarity to a partial image in the vicinity to the first plurality of points. If the first plurality of points has been established in the second perspective images, the second plurality of points in the first perspective images is the center point of partial images having the greatest similarity to partial images in the vicinity to the first plurality of points.

The image processor 100, based on the first plurality of points and the second plurality of points, calculates the difference in position of the target A between when the first perspective images were captured and when the second perspective images were generated. The image processor 100 outputs positioning information to the bed 600, based on the calculated difference.

The input/output device 200 may include, but is not limited to, a display 210 and an input device 220. The display 210 accepts image data from the image processor 100 and displays accepted image data. The image data includes, for example, a second perspective image generated based on volume data or a first perspective image captured by the radiographic imaging apparatus 400.

The input device 220 receives input of operations from a user and outputs information responsive to the operation input to the image processor 100. The input device 220 receives input of an operation specifying positions in either the first perspective images or the second perspective images displayed on the display 210. The input device 220 supplies coordinate information indicating the positions to the image processor 100. The input device 220 includes, for example, a pointing device such as a mouse and a touch panel, and a keyboard or the like. If the input device 220 has a touch panel, the display 210 and the input device 220 may be integrated into a single apparatus.

The treatment apparatus 500 performs treatment that subjects the target A to radiotherapy, proton therapy, particle radiotherapy or heavy ion radiotherapy. The treatment apparatus 500 may include, but is not limited to, a controller 510 and a plurality of ray irradiators 520. The controller 510 controls the plurality of ray irradiator 520 in the treatment apparatus 500. The controller 510 may, for example, be implemented by one or more processors, and executes a program to perform control operations based on the program. The controller 510 makes the ray irradiators 520 operable if the controller 510 detects that the bed 600 has moved the target A based on the difference. Each of the plurality of ray irradiators 520 irradiates toward the target A a radiation beam, a proton beam, a particle beam or a heavy ion beam based on user control when it goes into the movable state. The plurality of ray irradiators 520 are disposed so that the radiation beam, proton beam, particle beam irradiated or heavy ion beam from each of the ray irradiators 520 intersect at one point (isocenter).

The bed 600 may include, but is not limited to, a movable mount upon which the target A rests. The bed 600 moves the movable mount on which the target A rests, based on positioning information acquired from the image processor 100. This aligns a portion of the target A determined at the time of treatment planning with the isocenter. The movable mount is in the form of a stage, a chair, or the like.

Figure 2:
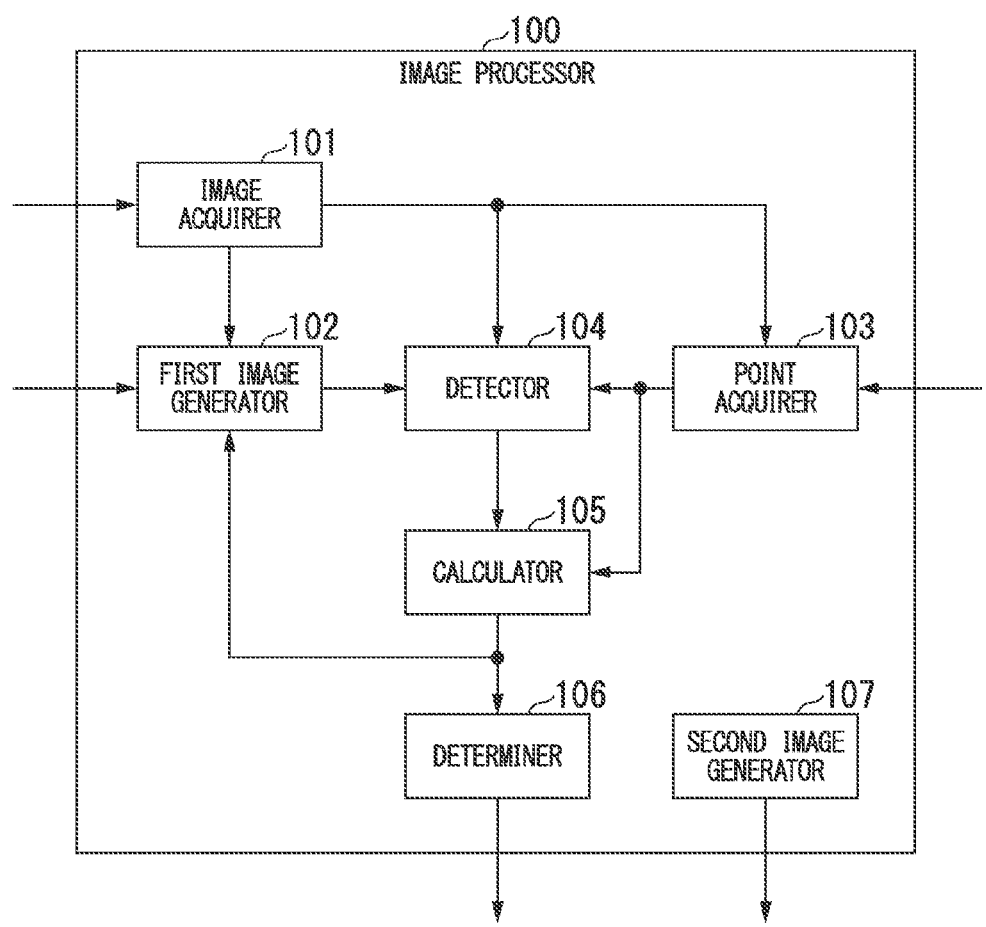
FIG. 2 is a block diagram illustrating the configuration of an image processor in accordance with the first embodiment.

FIG. 2 is a block diagram illustrating the configuration of the image processor 100 in the first embodiment. As shown in FIG. 2, the image processor 100 may include, but is not limited to, an image acquirer 101, a first image generator 102, a point acquirer 103, a detector 104, a calculator 105, a determiner 106, and a second image generator 107. The image processor 100 and the treatment system 10 in the first embodiment take the isocenter of the treatment apparatus 500 as the origin of the world coordinate system used in positioning. The three-dimensional coordinates used in the image processor 100 and treatment system 10 use the world coordinate system having the isocenter as the origin.

The X-ray images as the first perspective images and the second perspective image that are subjected to image processing in the image processor 100 will now be described.

An X-ray image is obtained when X-rays irradiated toward a subject from an X-ray source pass through the subject, reach an FPD and are then converted into pixel values in accordance with magnitude of the X-ray energy. X-ray detectors are disposed on a two-dimensional plane in the FPD, and the energy detected by each of the X-ray detectors is converted to a pixel value. Because the X-ray energy upon reaching the FPD is attenuated in response to tissues within the subject, the X-ray image is created from magnitude of energy of the X-ray which has penetrated through a target. The X-ray energy $P_j$ which has just reached at an X-ray detector on each pixel i∈$R^2$ in the X-ray image can be expressed by the following Expression (1).

$$P_i = P_0 \exp\{-\oint \mu(l,p)dl\} \quad (1)$$

In Expression (1), $P_0$ is the X-ray energy upon striking the subject, and μ(l,p) is the linear attenuation coefficient of an object at position l. The linear attenuation coefficient is a value varies in accordance with the X-ray energy P passing through a substance from the beam source. The value obtained by linearly integrating the linear attenuation coefficient of the substance in the path of the X-rays from the beam source up until reaching the X-ray detector disposed at pixel position i is the X-ray energy reaching the X-ray detector. Because the detection characteristics of the X-ray detectors are designed so as to be linear when the logarithm of $P_i$ is taken, an X-ray image is obtained by performing a linear conversion of the signal output from the X-ray detectors to pixel values. That is, the pixel values $T_i$ for each pixel of the X-ray image can be expressed by the following Expression (2), in which log($P_0$) is a constant.

$$T_i(P_0) = \log(P_i) = \text{Log}(P_0) - \oint \mu(l,p)dl \quad (2)$$

As noted above, each pixel of an X-ray image obtained by X-ray imaging are pixel values in accordance with sum of the products of the linear attenuation coefficient of the target A on the path of the X-ray irradiated from the ray source until reaching the X-ray detectors of the FDP.

Figure 3:
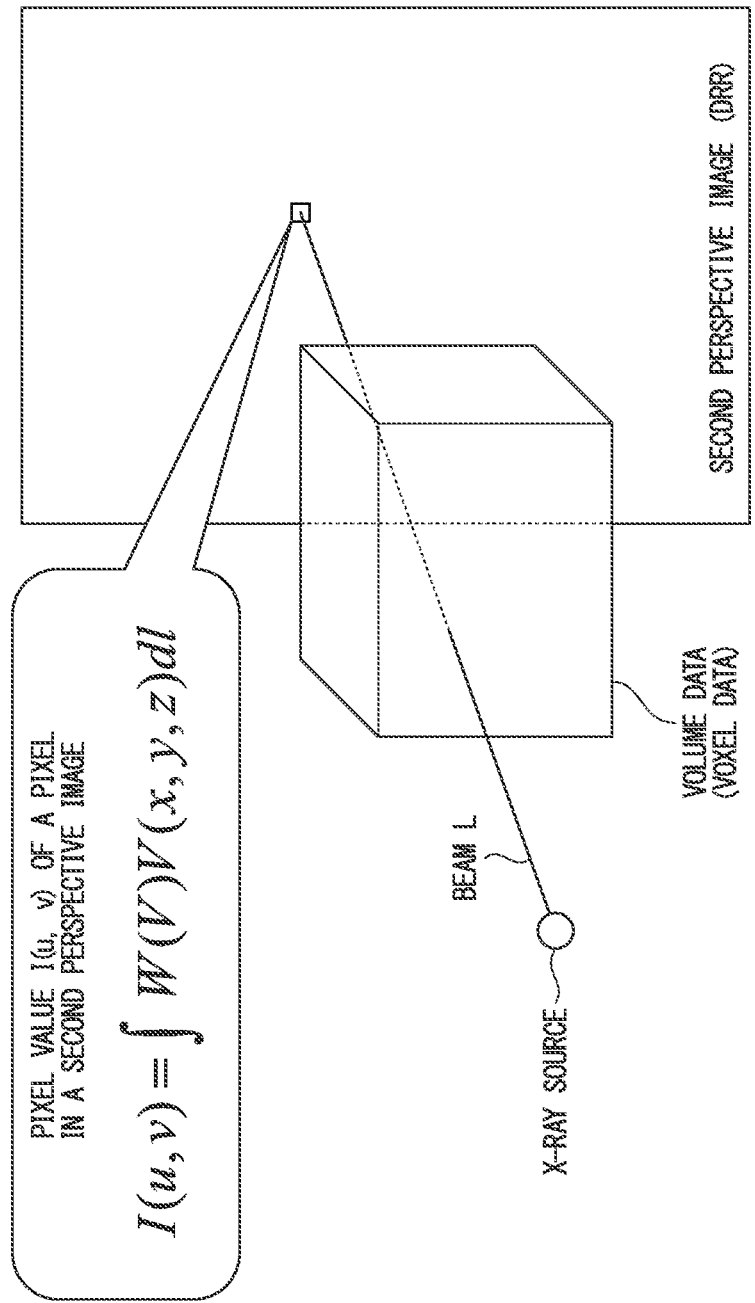
FIG. 3 is a drawing illustrating one of processes to be performed by the image processor of FIG. 2 when generating a perspective image.

The second perspective image (DRR: digitally reconstructed radiograph), for example when the target A expressed by volume data is placed virtually on the bed 600, is generated by a perspective view from an arbitrary direction. FIG. 3 illustrates the processing when the digitally reconstructed radiograph is generated. The coordinates in the three-dimensional coordinate system with the isocenter as the origin being (x, y, z), the two-dimensional coordinates in the digitally reconstructed radiograph are (u, v). The pixel value I(u, v) of a pixel at the coordinates (u, v) of the digitally reconstructed radiograph are calculated by the following Expression (3).

$$I(u,v) = \int W(V)V(x,y,z)dl \quad (3)$$

In Expression (3), V(x, y, z) is the value of the volume data at the coordinates (x, y, z) of the target A virtually disposed on the bed 600. The pixel value I(u, v) is obtained by integrating the values of the volume data on the beam L, as shown in Expression (3). W(V) is a weighting coefficient applied to the values of volume data. A digitally reconstructed radiograph in which specific values of volume data are emphasized can be generated by controlling the weighting coefficient W(V). Controlling the weighting coefficient W(V) can be done to emphasis tissue of interest when comparing a digitally reconstructed radiograph and an X-ray image, and to emphasis and improve the visibility of tissue of interest to the user.

The data value V(x, y, z) is a value based on the linear attenuation coefficient of the substance positioned at the location (x, y, z). Given this, if the digitally reconstructed radiograph is generated using the sum of the linear attenuation coefficients of the subject on the path of the beam L, the pixel value of the X-ray image, as shown by Expression (2), also is determined by the sum of the linear attenuation coefficients on the beam, so that the digitally reconstructed radiograph and the X-ray image are similar.

In order to generate a digitally reconstructed radiograph, it is necessary to determine the path L of the beam and the position of the volume data in the target A. When positioning the target A in the treatment system 10, the path L of the beam and the position in the target A for generating the digitally reconstructed radiograph are determined based on the path of the X-rays reaching the FPD in the radiographic imaging apparatus 400 when a first perspective image of the target A is captured during treatment.

Figure 4:
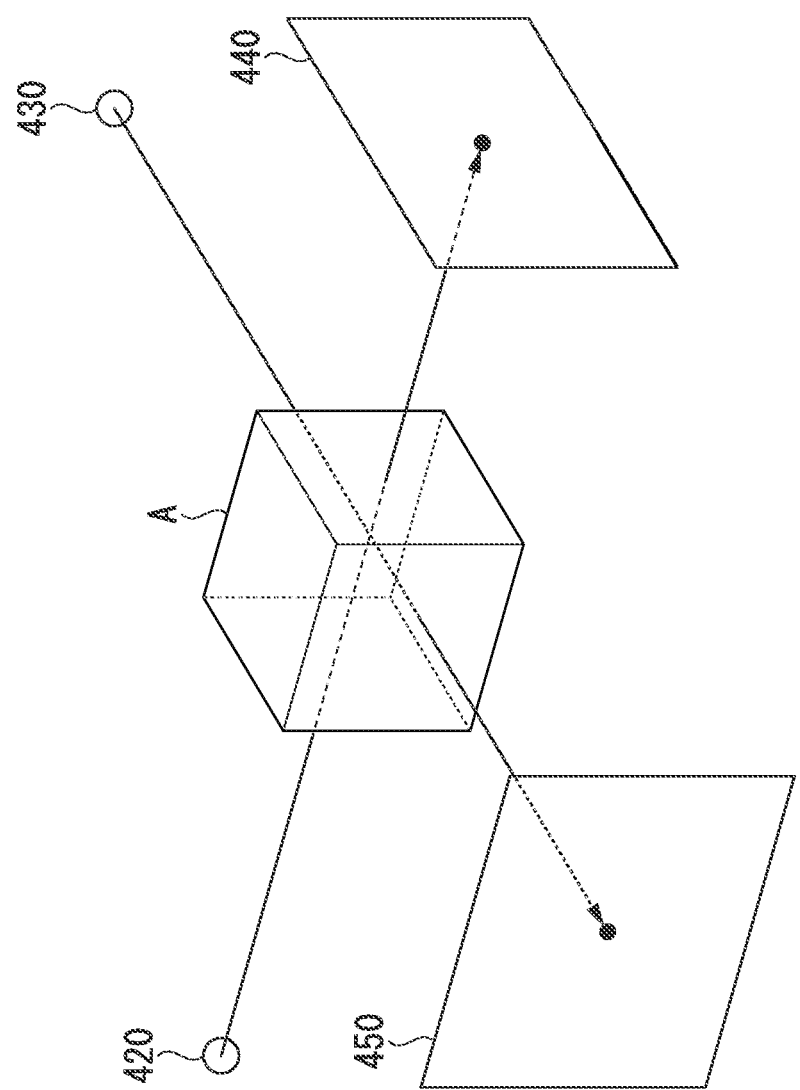
FIG. 4 is a drawing illustrating the disposition of a first ray irradiator, a second ray irradiator, a first ray detector, and a second ray detector in a radiographic imaging apparatus in accordance with the first embodiment.

FIG. 4 illustrates the disposition of the first ray irradiator 420, the second ray irradiator 430, the first ray detector 440, and the second ray detector 450 in a radiographic imaging apparatus 400 that captures first perspective images from two different directions. The X-ray irradiated from the first ray irradiator 420 passes through the target A and reaches the first ray detector 440. The first ray detector 440 generates a first perspective image based on X-ray energy passing through the target A. In the same manner, the X-ray irradiated from the second ray irradiator 430 passes through the target A and reaches the second ray detector 450. The second ray detector 450 generates another first perspective image based on X-ray energy passing through the target A.

In the radiographic imaging apparatus 400, the image capturing position is calibrated, a perspective projection matrix being determined for the purpose of coordinate conversion between the three-dimensional coordinate system established with respect to the treatment system and the two-dimensional coordinate system on the imaging planes in the first ray detector 440 and the second ray detector 450. In this manner, if the radiographic imaging apparatus 400 has been calibrated, because the positional relationships between the first ray irradiator 420 and first ray detector 440 and the second ray irradiator 430 and second ray detector 450 are known, the path L of the beam used in generating the second perspective images can be determined. Specifically, with the first ray irradiator 420 as the starting point of the path L, the ending points are taken to be each pixel on the imaging plane of the first ray detector 440. Similarly, with the second ray irradiator 430 as the starting point of the path L, the ending points are taken to be each pixel on the imaging plane of the second ray detector 450.

In this manner, if the second perspective image has been generated using the path L that is similar to the X-ray path when the first perspective image was captured, if the position of the volume data of the target A is the same as the position of the target A when the first perspective image was captured, the second perspective image and the first perspective image will be the most similar.

Figure 5:
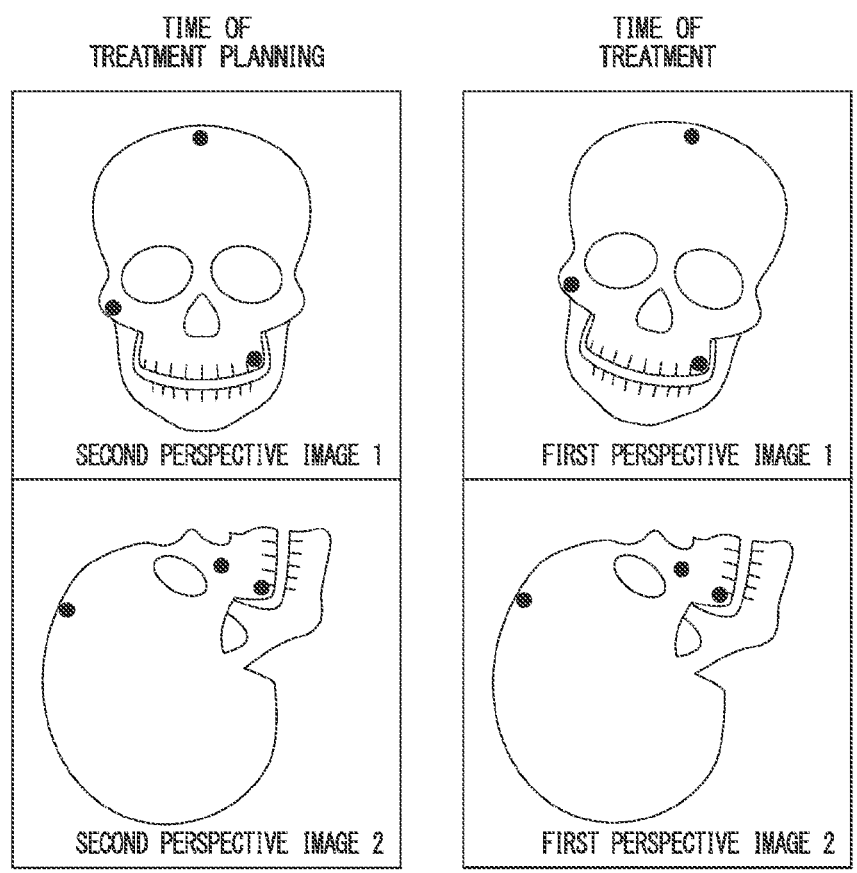
FIG. 5 is a drawing illustrating first perspective images and second perspective images in accordance with the first embodiment.

That is, when performing positioning, the user moves the volume data to achieve the greatest similarity between two first perspective images captured from different directions and two second perspective images to search for a position of coincidence and determine the difference. To move the volume data, it is necessary to determine six parameters of rotation about and parallel translation along the X, Y, and Z axes. In order to establish these six parameters, corresponding points in the first perspective images and the second perspective images are determined, as shown in FIG. 5, and the difference is calculated based on the corresponding points. FIG. 5 illustrates an example of corresponding points between the first perspective images and the second perspective images. In FIG. 5, black points indicate the corresponding points between at the time of treatment planning and at the time of treatment.

When points as a first plurality of points on either of the first perspective images or second perspective images are input, the image processor 100 detects the second plurality of points on the other image and calculates the difference. The image processor 100, based on the calculated difference, generates the second perspective images after the volume data of the target A has been moved. The image processor 100 once again detects the second plurality of points and calculates the difference. By repeating the second plurality of points detection and difference calculation, the image processor 100 eliminates the need for the user to input the second plurality of points and improves the positioning accuracy.

The image acquirer 101 acquires a pair of perspective images, these being the first perspective images of the target A captured in the radiographic imaging apparatus 400. The image acquirer 101 also acquires camera parameters of the first ray detector 440 that captured a first one of the first perspective images and another camera parameters of the second ray detector 450 that captured a second one of the first perspective images. The image acquirer 101 supplies the acquired pair of first perspective images to the detector 104. The image acquirer 101 supplies the two acquired camera parameters to the first image generator 102 and the point acquirer 103.

The first image generator 102 reads out volume data from the database 310 of the planning apparatus 300. The first image generator 102 acquires the two camera parameters from the image acquirer 101 and acquires the difference from the calculator 105. The first image generator 102 generates a second perspective image for each camera parameters, based on the volume data, the difference, and the two camera parameters. The difference is a value calculated by the calculator 105, based on the pair of first perspective images and the pair of second perspective images generated for each camera parameters. At the first time the first image generator 102 generates the second perspective images, there will be set zero the initial value of the difference. The first image generator 102 supplies to the detector 104 the generated pair of second perspective images.

The point acquirer 103 acquires from the input/output device 200 two-dimensional coordinates in images of a group of points that include points corresponding to at least three positions in the target A established by the user in the first perspective images or second perspective images. In the description to follow, points established by the user are the first plurality of points. The points established by a user to be characteristic in one of the first perspective images and the second perspective images, or special points in one of the first perspective images and the second perspective images are, for example, selected as the first plurality of points. In either of the cases of establishing the first plurality of points in the first perspective image and of establishing the first plurality of points in the second perspective image, points corresponding to the positions in the target A in images from different directions are established.

The first plurality of points included in the group of points acquired by the point acquirer 103 are points indicating the same positions in the target A in first perspective images or second perspective images captured from two different directions. For this reason, it is possible to calculate the three-dimensional position in the target A from the positions of each first plurality of points in the following manner.

The position of a first plurality of points in an image captured by the radiographic imaging apparatus 400 with a known projection matrix P included in the camera parameters is taken to be the vector x=(x, y, 1). If the position in the three-dimensional space of the target A at the first plurality of points position is taken to be the vector X=(X, Y, Z, 1), the following Expression (4) obtains.

$$\lambda x = PX \qquad (4)$$

In Expression (4), $\lambda$ is a constant representing the indeterminateness of the scale multiplier. In this case, if the vectors $x_1$ and $x_2$, which are the same positions in the target A in images captured from two different directors are specified, the simultaneous expressions of the following Expressions (5) obtain.

$$\begin{cases} \lambda_1 x_1 = P_1 X \\ \lambda_2 x_2 = P_2 X \end{cases} \qquad (5)$$

In Expressions (5), $P_1$ and $P_2$ are projection matrices when imaging from two different directions, and $\lambda_1$ and $\lambda_2$ are constants indicating the indeterminateness of the scale multiplier. The three-dimensional coordinates of the first plurality of points can be obtained by solving the Expressions (5) for the vector X. The point acquirer 103 calculates the three-dimensional coordinate of each of the first plurality of points included in the acquired group of points. The point acquirer 103 supplies coordinate information, including the three-dimensional coordinate of each of the first plurality of points, to the detector 104 and the calculator 105.

The point acquirer 103 may acquire the three-dimensional coordinates of a group of points in the target A used in a past treatment. The point acquirer 103 may acquirer points in a cross-sectional view of the target A generated based on volume data, so that the point acquirer 103 uses the acquired points as the first plurality of points. The point acquirer 103 may further acquire three-dimensional coordinates based on the volume data. Even if the position of the point group is acquired on three-dimensional coordinates, the point acquirer 103 can acquire a point on the image by performing conversion to two-dimensional coordinates in the image based on the Expressions (5). Because the therapy of the target A by the treatment system 10 is often performed a plurality of times, the point acquirer 103 may acquire a first plurality of points used in a past treatment.

The detector 104 detects a second plurality of points corresponding one-to-one to the first plurality of points included in the point group acquired from the point acquirer 103. The detector 104 extracts, for each point in the first plurality of points, partial images in the vicinity of the first plurality of points, using a rectangular window having a prescribed size with the first plurality of points as those own centers. If the first plurality of points is in the first perspective images, the detector 104 searches in the second perspective images for the partial image having the greatest similarity to the extracted partial images. The detector 104 sets the center of the detected partial images in the second perspective images as the corresponding point corresponding to the first plurality of points. If the first plurality of points is in the second perspective images, the detector 104 searches in the first perspective images for the partial image having the greatest similarity to the extracted partial image. The detector 104 sets the center of the detected partial image in the first perspective images as the corresponding point corresponding to the first plurality of points.

The detector 104 calculates the similarity using, for example, normalized cross correlation. The detector 104 may use other image characteristic features for calculating the similarity. For example, the detector 104 may use a characteristic feature based on a luminance gradient, an SIFT characteristics feature, an LBP characteristic feature, or a vector-type similarity characteristic feature for calculating the similarity. If a vector-type characteristic feature is used, the greater the similarity is, the smaller is the distance between vectors.

The detector 104 calculates the three-dimensional coordinate of each of the second plurality of points using the Equations (5). The detector 104 supplies coordinate information including the three-dimensional coordinates of the second plurality of points to the calculator 105.

The calculator 105 calculates the difference, based on the coordinate information of the first plurality of points acquired by the point acquirer 103 and the coordinate information of each second plurality of points calculated by the detector 104. The calculator 105, based on the first plurality of points and the second plurality of points in the four images of the first perspective images and the second perspective images captured from two different directions, calculates the position of the target A when the first perspective image was captured and the position of the target A when the second perspective image was generated.

The calculator 105 acquires a three-dimensional position $X_i$ of the target A expressed with the volume data and another three-dimensional position $Y_i$, of the target A. The calculator 105 calculates the difference, wherein the difference is at a time the target A is moved from the three-dimensional position $X_i$ to the three-dimensional position $Y_i$. If there is performed a rigid body movement of the target A, including rotation and parallel translation in the three-dimensional space, then the following Expression (6) is satisfied.

$$Y_i = RX_i + t \qquad (6)$$

In Expression (6), the matrix R is a 3-row, 3-column rotation matrix, and the vector t is a 3-row, 1-column parallel translation vector. The matrix R and the vector t are the difference calculated by the calculator 105. With Expression (6) obtaining with respect to the three-dimensional positions $X_i$, and $Y_i$ (i=1, 2, ..., N) of the first plurality of points and the second plurality of points acquired as corresponding points, the difference is calculated with those equations taken to be simultaneous equations.

With the center of gravity of the three-dimensional position $X_i$ (i=1, 2, ..., N) taken as $\bar{X}$ and that of the three-dimensional position $Y_i$ (i=1, 2, ..., N) taken as $\bar{Y}$, the parallel translation vector t is represented as in the following Expression (7). If the rotation matrix R is found, the parallel translation vector t is determined. Note that $\bar{X}$ is used as a convenience in representing the parameter "X bar" and other parameters with bars over them are indicated with the same symbol $\bar{\phantom{X}}$.

$$t = \bar{Y} - R\bar{X} \qquad (7)$$

In this case, if we let $X'_i = X_i - \bar{X}$ and $Y'_i = Y_i - \bar{Y}$, we calculate the rotation matrix R resulting in the following Expression (8). The problem of finding such a matrix R is known as the orthogonal Procrustes problem, for which various methods of solution exist. The calculator 105 uses any known method of solution to calculate the rotation matrix R. The calculator 105 substitutes the calculated rotation matrix R into Expression (7) and calculates the parallel translation vector t. The calculator 105 supplies the determiner 106 and the first image generator 102 with the difference, which includes the rotation matrix R and the parallel translation vector t.

$$\min \|Y'_i - RX'_i\|^2 \qquad (8)$$

The determiner 106 determines whether or not the difference calculated by the calculator 105 satisfies a pre-established criterion. If the difference satisfies the criterion, the determiner 106 supplies positioning information including the difference to the bed 600. If the difference does not satisfy the criterion, the determiner 106 makes the first image generator 102 generate a second perspective image, the detector 104 detect the second plurality of points, and the calculator 105 calculate the difference.

The criterion with respect to the difference will now be described. If the similarity between the second perspective image and the first perspective image is at least a pre-established threshold, the determiner 106 determines the difference to satisfy the criterion. The second perspective images used in the determination is the second perspective images generated by the first image generator 102 from an updated one of the volume data, which is different by the difference from a previous one of the volume data. The calculation of the similarity between the first perspective images and the second perspective images is done using, for example, the normalized cross correlation. In lieu of calculating the normalized cross correlation, the similarity may be calculated using the mutual information amount, the similarity of the histograms of the pixel values of each image may be calculated, or the pixel values of each image may be normalized and the square error may be calculated. Additionally, the similarity may be calculated by an image characteristic based on the gradient of pixel values in each of the images.

In lieu of calculating the similarity of the overall image when calculating the similarity between the first perspective images and the second perspective images, the determiner 106 may calculate the localized similarity of partial images having a certain size that include the first plurality of points and the second plurality of points. That is, the determiner 106 may use the localized similarity between partial images in the vicinity of each of the first plurality of points and the second plurality of points, respectively, as the similarity between the first perspective images and the second perspective images, wherein the second perspective image has been generated from an updated one of the volume data which is different by the difference from a previous one of the volume data and the first perspective image.

If the similarity between the first perspective images and the second perspective images is lower than the similarity calculated at the time of the previous determination, the determiner 106 stops the repeat of calculation of the difference and supplies the bed 600 with positioning information including the difference from the previous time.

In lieu of using the similarity between the second perspective images and the first perspective images as the criterion for the difference, the rotational angle about the X, Y, and Z axes based on the rotation matrix R and the size of the parallel translation vector t that are included in the difference may be calculated. When this is done, the determiner 106 determines whether or not every rotational angle and size is not greater than a prescribed threshold. If each rotational angle and size is not greater than the threshold, the determiner 106 supplies the bed 600 with positioning information including the difference. If any of the rotational angles and sizes is larger than the threshold, the determiner 106 makes the first image generator 102 generate the second perspective images, the detector 104 detect the second plurality of points, and the calculator 105 calculate the difference.

In lieu of the determination using the similarity between the second perspective images and the first perspective images or using the difference, the determiner 106 may determine whether or not the difference has been calculated a prescribed number of times. When the difference is repeatedly calculated the prescribed number of times, the determiner 106 supplies the bed 600 with positioning information including the last calculated difference. The determiner 106 may establish the number of repetitions in accordance with the tissue of the target A being projected in the first perspective images. In the case in which the determiner 106 establishes the number of repetitions, the determiner 106 distinguishes the tissue of the target A to be projected based on the volume data value V (x, y, z) used when generating the second perspective images. Distinguishing the tissue of the target A may be done based on patterns of values in the volume data. The determiner 106 may distinguish the tissue of the target A based on information included in DICOM (Digital Imaging and Communication in Medicine) data or information input by the user. For example, the determiner 106 calculates the area of a region of a bone in the first perspective image and, if the proportion that the region of the bone occupies in the second perspective image is at least a pre-established threshold, the determiner 106 makes the number of repetitions smaller than a reference number of times. If the proportion that the region of the bone occupies in the second perspective image is smaller than the pre-established threshold, the determiner 106 makes the number of repetitions greater than the standard number of times. In the case of acquiring a first perspective images using an X-ray imaging apparatus, because the larger is the bone the higher is the contrast in the first perspective images and the higher is the accuracy of the second plurality of points, resulting in acquisition of a highly accurate difference even with a small number of repetitions. The determiner 106 may make the number of repetitions smaller, the higher is the contrast in at least one of the second perspective images and the first perspective images.

The second image generator 107 generates image data that includes the first perspective images acquired by the image acquirer 101, the second perspective image generated by the first image generator 102, the first plurality of points acquired by the point acquirer 103, and the second plurality of points detected by the detector 104. The second image generator 107 may generate image data in which the first plurality of points and the second plurality of points are overlaid onto the first perspective images or the second perspective images. The second image generator 107 supplies the generated image data to the input/output device 200.

Figure 6:
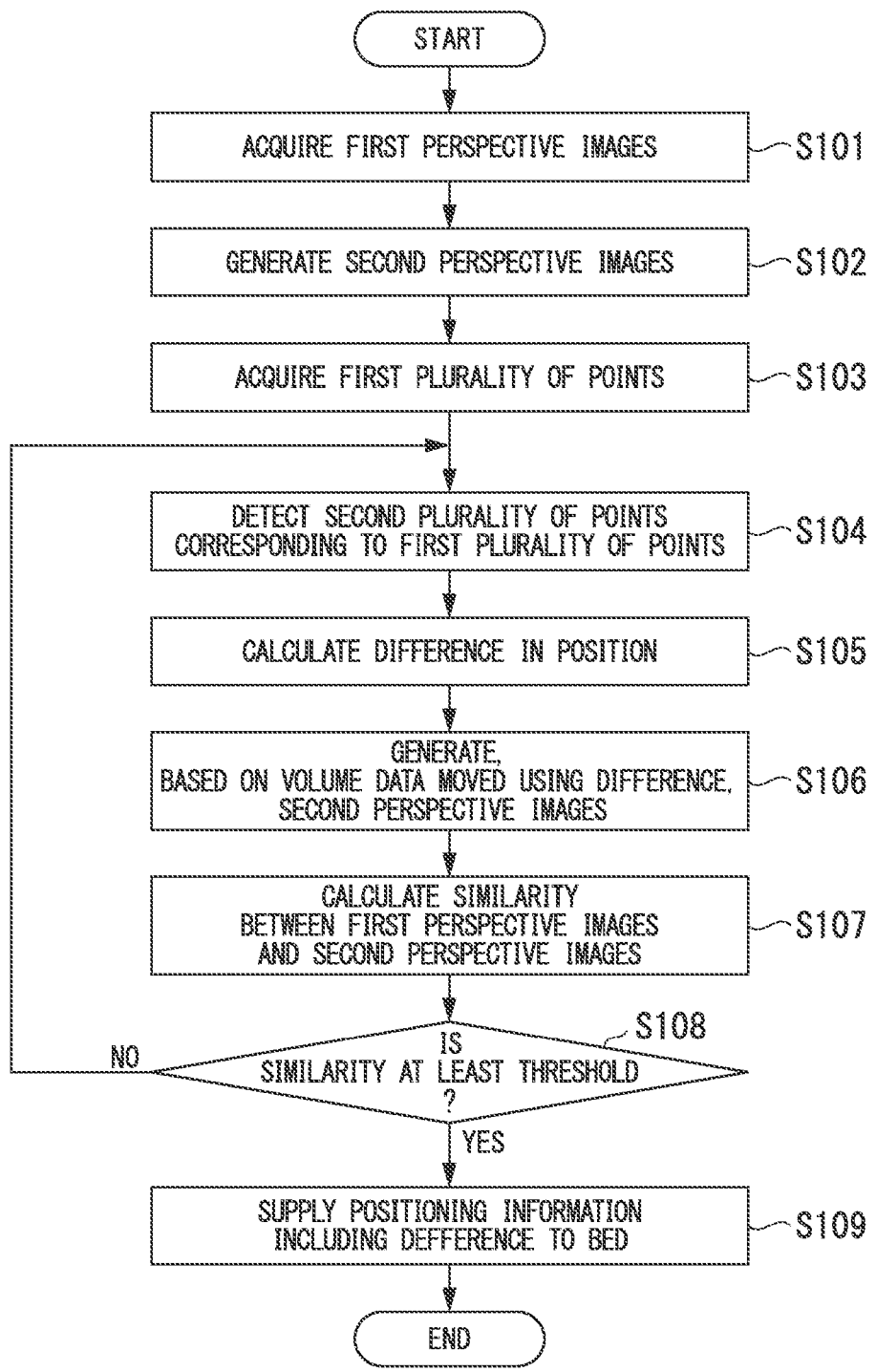
FIG. 6 is a flowchart illustrating a series of processes, including a positional-difference calculation process, performed by the image processor of FIG. 2.

FIG. 6 is a flowchart illustrating the difference calculation processing performed by the image processor 100. In the image processor 100, when the difference calculation processing starts, the image acquirer 101 acquires from the radiographic imaging apparatus 400 the first perspective images captured from different directions and camera parameters with respect to each the first perspective image (step S101).

The first image generator 102, based on volume data of the target A and the camera parameters acquired by the image acquirer 101, generates the second perspective image corresponding to each of the first perspective images (step S102).

The point acquirer 103 acquires at least three user-specified points as the first plurality of points (step S103).

The detector 104 detects points in either the first perspective images or the second perspective images corresponding one-to-one to the first plurality of points. The detector 104 takes the detected points to be the second plurality points (step S104).

The calculator 105, based on the three-dimensional coordinate of each point of the first plurality of points and the three-dimensional coordinate of each point of the second plurality of points, calculates the difference in position of the target A between when the first perspective images were captured and when the second perspective images were generated (step S105).

The first image generator 102, based on the volume data moved using the difference and the camera parameters, generates the second perspective images corresponding to the first perspective images (step S106).

The determiner 106 calculates the similarity between the second perspective images generated at step S106 and the first perspective images acquired at step S101 (step S107). The determiner 106 determines whether or not the calculated similarity is at least the threshold (step S108).

If the similarity is not at least the threshold (NO at step S108), the determiner 106 determines that the processing returns to step S104 for reputation of steps S104 through step S108.

If the similarity is at least the threshold (YES at step S108), the determiner 106 supplies positioning information including the difference to the bed 600 (step S109) and terminates the difference calculation processing.

When the image processor 100 in the first embodiment acquires the first plurality of points indicating positions of the target A in the first perspective images, the image processor 100 detects the second plurality of points corresponding one-to-one to the first plurality of points in the second perspective images. The image processor 100 calculates the difference based on the first plurality of points and the second plurality of points.

When the image processor 100 in the first embodiment acquires a first plurality of points indicating positions of the target A in the second perspective images, the image processor 100 detects the second plurality of points corresponding to the first plurality of points in the first perspective images. The image processor 100 calculates the difference based on the first plurality of points and the second plurality of points.

In this manner, the image processor 100 calculates the difference in position of the target A between when the first perspective images were captured and when a treatment plan was established based on the volume data. The calculation is made without setting points on the target A in both the first perspective images and the second perspective images. This eliminates the need for the user to determine points, in the both the first perspective images and the second perspective images, indicating a specific positions of the target A, thereby shortening the time required for positioning in the treatment system 10. The image processor 100 repeatedly generates the second perspective images and calculates the difference until the similarity between the first perspective images and the second perspective images satisfies the criterion, thereby improving the accuracy of the difference and that the accuracy of positioning.

The image processor 100 determines to repeatedly calculate the difference based on the similarity between the first perspective images and the second perspective images until it is possible to improve the accuracy of the calculated difference.

The image processor 100 determines to terminate the repeat of calculation of the difference if the similarity between partial images in the vicinity of the first plurality of points and the second plurality of points satisfies a criterion, thereby improving the accuracy of second plurality of points, reducing the amount of the calculation, and shortening the necessary time for positioning.

In the image processor 100, the determiner 106 determines the number of repetitions in accordance with the tissue such as bone of the target A projected in the second perspective images, thereby shortening the necessary time for positioning.

Second Embodiment

Figure 7:
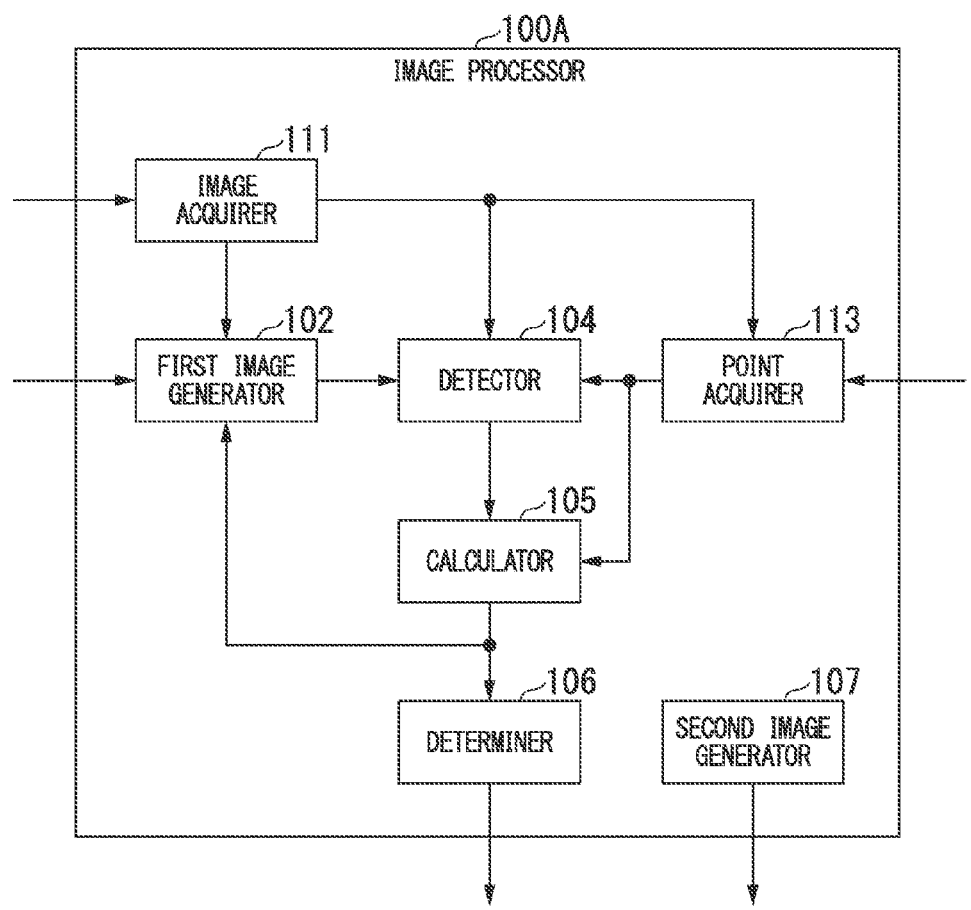
FIG. 7 is a block diagram illustrating the configuration of an image processor in accordance with a second embodiment.

FIG. 7 is a block diagram illustrating the configuration of the image processor 100A in the second embodiment. As shown in FIG. 2, the image processor 100A may include, but is not limited to, an image acquirer 111, the first image generator 102, a point acquirer 113, the detector 104, the calculator 105, the determiner 106, and the second image generator 107. The image processor 100A of the second embodiment is used in place of the image processor 100 in the treatment system 10 shown in FIG. 1. In the image processor 100A, the same configurations or structural elements as those of the image processor 100 of the first embodiment are assigned with the same reference numerals and the duplicate descriptions thereof will be omitted.

The image acquirer 111 acquires a pair of perspective images, these being the first perspective images of the target A captured in the radiographic imaging apparatus 400. The image acquirer 111 also acquires camera parameters of the first ray detector 440 that captures a first one of the first perspective images and another camera parameters of the second ray detector 450 that captures a second one of the first perspective images. The image acquirer 111 changes the resolution of the first perspective images so that the actual dimension per pixel in the image of the target A indicated by the second perspective images generated by the first image generator 102 matches the actual dimension per pixel in the image of the target A indicated by the first perspective image. The image acquirer 111 also applies the smoothing filter to the first perspective images acquired by changing their resolution so as to smooth the pixel values. The image acquirer 111 supplies the detector 104 with the pair of the first perspective images that have been subjected to a change of resolution and smoothing filtering. The image acquirer 111 also supplies the two camera parameters to the first image generator 102 and the point acquirer 113.

The point acquirer 113, in addition to the operation performed by the point acquirer 103 in the first embodiment, performs operation to acquire from the input/output device 200 correction information that includes instructions to correct the position of the second plurality of points detected by the detector 104. The instruction to correct the second plurality of points t is acquired by the user verifying the first perspective images and the second perspective images onto which the second plurality of points is overlaid. The input device 220 of the input/output device 200 gives the point acquirer 113 the correction information by user. The point acquirer 113 supplies the acquired correction information to the calculator 105. If correction information has been supplied, the calculator 105 changes the position of the second plurality of points in one of the first perspective images and the second perspective images based on the correction information, and then the calculator 105 calculates the difference based on the first plurality of points and the second plurality of points which has been changed in position.

Figure 8:
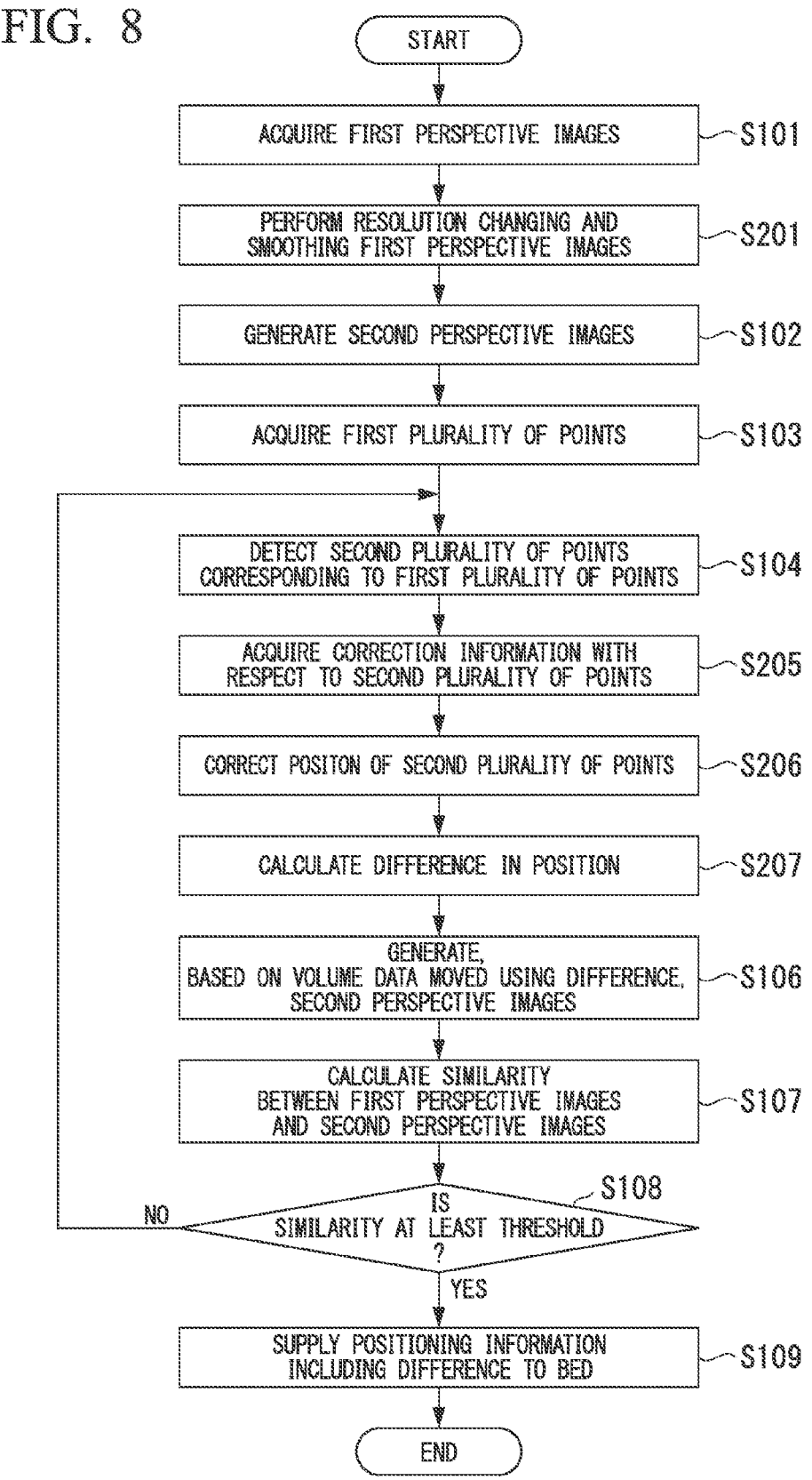
FIG. 8 is a flowchart illustrating a series of processes, including a positional-difference calculation process, performed by the image processor of FIG. 7.

FIG. 8 is a flowchart illustrating the difference calculation processing performed by the image processor 100A. In the image processor 100A, when the difference calculation processing starts, the image acquirer 111 acquires from the radiographic imaging apparatus 400 the first perspective images captured from different directions and camera parameters with respect to each first perspective image (step S101). The image acquirer 111 performs resolution changing and smoothing processing with respect to each of the first perspective images, so that the actual dimension per pixel of the first perspective images matches that of the second perspective images (step S201).

The first image generator 102, based on volume data of the target A and the camera parameters acquired by the image acquirer 111, generates the second perspective image corresponding to each of the first perspective images (step S102).

The point acquirer 103 acquires at least three user-specified points as the first plurality of points (step S103).

The detector 104 detects points in either the first perspective images or the second perspective images corresponding one-to-one to the first plurality of points. The detector 104 takes the detected points to be the second plurality points (step S104).

The point acquirer 113 acquires correction information with respect to the position of the second plurality of points detected by the detector 104 (step S205).

The calculator 105, based on the correction information, corrects the position of the second plurality of points detected by the detector 104 (step S206).

The calculator 105, based on the three-dimensional coordinate of each point in the first plurality of points and the three-dimensional coordinate of each point in the second plurality of points having been corrected in position, calculates the difference in position of the target A between when the first perspective images were captured and when the second perspective images were generated (step S207).

The first image generator 102, based on the volume data moved using the difference and the camera parameters, generates second perspective images corresponding to the first perspective images (step S106).

The determiner 106 calculates the similarity between the second perspective images generated at step S106 and the first perspective images acquired at step S101 (step S107). The determiner 106 determines whether or not the calculated similarity is at least the threshold (step S108).

If the similarity is not at least the threshold (NO at step S108), the determiner 106 returns the processing returns to step S104 for reputation of step S104 thorough step S108.

If the similarity is at least the threshold (YES at step S108), the determiner 106 supplies positioning information including the difference to the bed 600 (step S109) and terminates the difference calculation processing.

When the image processor 100A in the second embodiment acquires the first plurality of points indicating positions of the target A in the first perspective images, the image processor 100A detects the second plurality of points corresponding one-to-one to the first plurality of points in the second perspective images. The image processor 100A supplies to the input/output device 200 with image data including an image in which the first plurality of points is overlaid onto the first perspective image and another image in which the second plurality of points is overlaid onto the second perspective images. The user verifies the image data displayed on the input/output device 200 to determine that the second plurality of points are out of respective acceptable-regions in the second perspective images. The acceptable-regions are regions in which the second plurality of points should respectively be positioned so as to permit the user to identify correspondence between the first plurality of points and the second plurality of points. If the user determines that the second plurality of points are out of the respective acceptable-regions, then the user enters via the input device 220 instructions to correct a position of at least one of the second plurality of points in the image displayed by the display 210. Upon the instructions entered, the image processor 100A corrects the position of the second plurality of points. The instructions are included in the correction information mentioned above. Based on the first plurality of points and the second plurality of points, the later of which has been corrected in those positions, the image processor 100A calculates the difference in position of target A between when the first perspective images were captured and when the second perspective images were generated. The user verifies and corrects the second plurality of points to improve the accuracy in position of the second plurality of points when there are many similar partial images in the second perspective images. This enables the image processor 100A to improve the accuracy of calculating the difference and to improve the accuracy of positioning. In the same manner, the image processor 100A acquires a first plurality of points indicating positions in the target A in a second perspective image to improve the accuracy of the calculated value of the difference and improve the accuracy of positioning.

The image processor 100A also performs a change in resolution of the first perspective images to adjust the actual dimension per pixel in the first perspective images with respect to the actual dimension per pixel in the second perspective images. This improves the similarity between the first perspective images and the second perspective images resulting in an improved accuracy in determining whether the series of processes is repeated or terminated. As a result, the image processor 100A can improve the accuracy of calculating the difference.

The image processor 100A changes the resolution of the first perspective images and performing smoothing on the first perspective images. If the resolution of the second perspective images is lower than the resolution of the first perspective images, this causes a plurality of pixels in the first perspective image to correspond to one pixel in the second perspective image. In this case, a pixel value in the second perspective images is compared with a plurality of pixel values in the first perspective images, and there occurs an undesired degree of variations of the calculated value of the similarity between the second perspective images and the first perspective images. Smoothing of first perspective images having been changed in resolution is performed to suppress the above-noted undesired degree of variations, resulting in an improvement in the accuracy of determination using the similarity.

Although the above-noted embodiments have been described for the case in which the first plurality of points is established in either first perspective images or second perspective images, a first plurality of points may be established in both the first perspective image and the second perspective image. When this is done, the detector 104 detects the second plurality of points corresponding one-to-one to the first plurality of points in the first perspective image and the second perspective image.

If the first plurality of points acquired by the point acquirer have more than three points, there are available the RANSAC method or the least median method (Lmeds) as a robust estimation method to estimate the posture of the target A. The image processor calculates the difference based on the estimated posture of the target A.

According to the image processor, the treatment system and the image processing method of at least one embodiment described above, the detector, the calculator and the determiner are provided to not only improve the accuracy of positioning but also shorten the necessary time for positioning. The detector is provided to detect a second plurality of points corresponding one-to-one to a first plurality of points established by a user. The calculator is provided to calculate, based on at least the first plurality of points and the second plurality of points, the difference in position of target A between when first perspective images were captured and when second perspective images were generated from the volume data of target A. The determiner is provided to determine whether or not the difference is in a prescribed range and, if it does not, causes repeated second plurality of points detection and difference calculation.

Further, each of the above image processors may be implemented by a general semiconductor integrated circuit, or a customizable electronic circuit such as an FPGA (field programmable gate array). Also each of the above image processors may be implemented by a processor and a memory that stores processor-executable instructions that, when executed by the processor, to cause the processor to perform the above-described acts or operations for the above-described image processing.

In other cases, one or more programs for the image processor of each of the above embodiments to perform the above-described acts or operations for the above-described image processing may be stored in a computer-readable recording medium, so that a computer system can read and execute the program stored in the computer-readable recording medium, thereby performing the positioning process.

Here, the "computer system" may include software such as an OS and one or more applications and hardware such as any peripheral device. Additionally, the "computer system" may include a WWW system that provides homepage providing or displaying environments.

Further, the "computer-readable storage medium" may include any non-transitory computer-readable storage mediums such as a storage device, such as a portable medium, for example, a flexible disk, a magneto optical disk, a ROM, or a CD-ROM, or a hard disk built in a computer system. Moreover, the computer-readable storage medium may also include a medium that temporarily stores a program, such as a volatile memory included in a computer system which serves as a server or client when the program is transmitted via a network such as the Internet, or a communication line such as a telephone line.

Additionally, the above program may be transmitted from a computer system storing that program in a storage device thereof to another computer system via a transmission medium or by carrier waves passing through a transmission medium. The "transmission medium" that transmits the program may include a medium having a function of transmitting information, such as a communication network, for example, the Internet, or a communication line, for example, a telephone line. Further, the above program may include a differential program in combination with the program already stored in the computer system.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processor comprising processing circuitry configured to at least:
    acquire a plurality of first perspective images, which have been captured from a target in at least two mutually different directions;
    generate from volume data of the target a plurality of second perspective images in the at least two mutually different directions;
    acquire a first plurality of points in one of the first perspective images and the second perspective images;
    detect a second plurality of points in the second perspective images corresponding to the first plurality of points if the first plurality of points is present in the first perspective images, and detect a second plurality of points in the first perspective images corresponding to the first plurality of points if the first plurality of points is present in the second perspective images;

calculate based on at least the first plurality of points and the second plurality of points, a difference in position of the target between when the first perspective images were captured and when the second perspective images were generated; and determine whether or not the difference is in a range, wherein the processing circuitry is configured to, if the difference is not in the range, generate updated ones of the second perspective images from an updated one of the volume data, which is different by the difference from a previous one of the volume data, wherein the processing circuitry is configured to, if the difference is not in the range, detect an updated one of the second plurality of points in one of the first perspective images and the updated ones of the second perspective images, and wherein the processing circuitry is configured to, if the difference is not in the range, calculate the difference based on at least the first plurality of points and the updated one of the second plurality of points.

2. The processor according to claim 1, wherein the processing circuitry is further configured to calculate a similarity between the first perspective images and the second perspective images, and determine whether or not the similarity calculated is at least a pre-established threshold to determine whether or not the difference is in the range.

3. The processor according to claim 1 wherein the processing circuitry is further configured to calculate a similarity between partial images including the first plurality of points or the second plurality of points in the first perspective images and second partial images including the first plurality of points or the second plurality of points in the second perspective images, and determine whether or not the similarity calculated is at least a pre-established threshold to determine whether or not the difference is in the range.

4. The processor according to claim 1, wherein the processing circuitry is further configured to determine the difference is the range if the difference is calculated a prescribed number of times.

5. The processor according to claim 4, wherein the processing circuitry is further configured to determine the prescribed number of times based on an image contrast of at least one of the first perspective images and the second perspective images.

6. The processor according to claim 5, wherein the processing circuitry is further configured to determine the prescribed number of times which is smaller as the image contrast is higher.

7. The processor according to claim 4, wherein the processing circuitry is further configured to identify a tissue of the target, where a projected image of the tissue is included in at least one of the first perspective images and the second perspective images, and determine the prescribed number of times in accordance with the tissue identified.

8. The processor according to claim 7, wherein the processing circuitry is further configured to calculate an area of bone in the projected target of at least one of the first perspective images and the second perspective image, and make the prescribed number of times smaller as the area is larger.

9. The processor according to claim 1, wherein the processing circuitry is further configured to calculate the similarity between the first perspective images and the updated ones of the second perspective images, and output the difference if the similarity calculated is lower than a similarity between the first perspective images and a previous ones of the second perspective images.

10. The processor according to claim 1, wherein the processing circuitry is further configured to perform smoothing of the first perspective image.

11. The processor according to claim 1, wherein the processing circuitry is further configured to make a change in resolution of the first perspective images to make the projected image of the tissue in the first perspective image be identical in dimension with the projected image of the tissue in the second perspective image.

12. The processor according to claim 1, wherein processing circuitry is further configured to receive the first plurality of points, the second plurality of points, the first perspective images and the second perspective images; and generate image data based on the first plurality of points, the second plurality of points, the first perspective images and the second perspective images.

13. A treatment system comprising:

a radiographic imaging apparatus that captures a plurality of first perspective images of a target from at least mutually different directions;

an image processor; and a display, wherein the image processor comprises processing circuitry configured to at least:

acquire the plurality of first perspective images from the radiographic imaging apparatus;

generate from volume data of the target a plurality of second perspective images in the at least two mutually different directions;

acquire a first plurality of points in one of the first perspective images and the second perspective images;

detect a second plurality of points in the second perspective images corresponding one-to-one to the first plurality of points if the first plurality of points is present in the first perspective images, and detect a second plurality of points in the first perspective images corresponding one-to-one to the first plurality of points if the first plurality of points is present in the second perspective images;

calculate, based on at least the first plurality of points and the second plurality of points, a difference in position of the target between when the first perspective images were captured and when the second perspective images were generated; and determine whether or not the difference is in a range, wherein the processing circuitry is configured to, if the difference is not in the range, generate updated ones of the second perspective images from an updated one of the volume data, which is different by the difference from a previous one of the volume data, wherein the processing circuitry is configured to, if the difference is not in the range, detect an updated one of the second plurality of points in one of the first perspective images and the updated ones of the second perspective images, wherein the processing circuitry is configured to, if the difference is not in the range, calculate the difference based on at least the first plurality of points and the updated one of the second plurality of points, and wherein the display displays the first perspective images and the second perspective images.

14. The system according to claim 13, wherein the target volume data is acquired by imaging the target using an X-ray CT apparatus.

15. The system according to claim 13,
wherein the processing circuitry is further configured to generate image data in which the first plurality of points and the second plurality of points are overlaid onto the first perspective images and the second perspective images, and supply the image data to the display, wherein the system further comprises an input device for giving the image processor instructions to correct a position of at least one of the second plurality of points in the image displayed by the display, and wherein the processing circuitry is further configured to calculate an updated one of the second plurality of points based on the instructions, and calculate the difference based on at least the first plurality of points and the updated one of the second plurality of points.

16. The system according to claim 13, further comprising:
one or more irradiators that irradiates radiation to the target.

17. The system according to claim 13, further comprising:
a bed that includes a movable mount for the target; and
a treatment apparatus for irradiating the target with radiation, wherein the bed receives the difference from the image processor, and the bed, based on the difference, moves the movable mount for irradiation to the target.

18. An image processing method comprising:
acquiring a plurality of first perspective images, which have been captured from a target in at least two mutually different directions;
generating from volume data of the target a plurality of second perspective images in the at least two mutually different directions;
acquiring a first plurality of points in one of the first perspective images and the second perspective images;
detecting a second plurality of points in at least one of:
  a) the second perspective images corresponding to the first plurality of points if the first plurality of points is present in the first perspective images; and
  b) the first perspective images corresponding to the first plurality of points if the first plurality of points is present in the second perspective images;
calculating, based on at least the first plurality of points and the second plurality of points, a difference in position of the target between when the first perspective images were captured and when the second perspective images were generated;

determining whether or not the difference is in a range;
generating updated ones of the second perspective images from an updated one of the volume data, which is different by the difference from a previous one of the volume data, if the difference is not in the range;
detecting an updated one of the second plurality of points in one of the first perspective images and the updated ones of the second perspective images, if the difference is not in the range; and
calculating the difference based on at least the first plurality of points and the updated one of the second plurality of points, if the difference in not in the range.

19. An image processor comprising:
a processor; and
a memory that stores processor-executable instructions that, when executed by the processor, cause the processor to:
acquire a plurality of first perspective images, which have been captured from a target in at least two mutually different directions;
generate from volume data of the target a plurality of second perspective images in the at least two mutually different directions;
acquire a first plurality of points in one of the first perspective images and the second perspective images;
detect a second plurality of points in at least one of:
  a) the second perspective images corresponding to the first plurality of points if the first plurality of points is present in the first perspective images; and
  b) the first perspective images corresponding to the first plurality of points if the first plurality of points is present in the second perspective images;
calculate, based on at least the first plurality of points and the second plurality of points, a difference in position of the target between when the first perspective images were captured and when the second perspective images were generated;
determine whether or not the difference is in a range;
generate updated ones of the second perspective images from an updated one of the volume data, which is different by the difference from a previous one of the volume data, if the difference is not in the range;
detect an updated one of the second plurality of points in one of the first perspective images and the updated ones of the second perspective images, if the difference is not in the range; and
calculate the difference based on at least the first plurality of points and the updated one of the second plurality of points, if the difference in not in the range.

* * * * *